US009121836B2

(12) United States Patent
Simons et al.

(10) Patent No.: US 9,121,836 B2
(45) Date of Patent: Sep. 1, 2015

(54) RETRONASAL DEVICE AND METHOD

(71) Applicant: Givaudan S.A., Vernier (CH)

(72) Inventors: Christopher Todd Simons, Wyoming, OH (US); Joseph Andrew Kaiser, Alexandria, KY (US); Matthew Charles Burland, Cincinnati, OH (US); Mark Thirston Yates, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 323 days.

(21) Appl. No.: 13/795,532

(22) Filed: Mar. 12, 2013

(65) Prior Publication Data

US 2013/0319079 A1 Dec. 5, 2013

Related U.S. Application Data

(60) Provisional application No. 61/652,623, filed on May 29, 2012.

(51) Int. Cl.
*A61M 15/00* (2006.01)
*A61B 5/00* (2006.01)
*G01N 33/00* (2006.01)
*A61M 15/08* (2006.01)
*A61M 16/04* (2006.01)

(52) U.S. Cl.
CPC .......... *G01N 33/0011* (2013.01); *A61B 5/4011* (2013.01); *A61M 15/08* (2013.01); *A61M 16/0493* (2014.02); *G01N 33/0001* (2013.01); *A61B 5/4017* (2013.01); *A61M 15/0021* (2014.02)

(58) Field of Classification Search
CPC ..... A61C 5/14; A61F 5/566; A61M 15/0021; A62B 9/06; B01F 2215/009; G01N 33/0001; G01N 1/2273; G01N 2001/2276
See application file for complete search history.

(56) References Cited

U.S. PATENT DOCUMENTS 803,475 A * 10/1905 Dennis ............................ 433/80
2,136,844 A * 11/1938 Firth et al. ................... 73/23.34
(Continued)

FOREIGN PATENT DOCUMENTS

FR 2661836 A1 * 11/1991
JP 2004/159675 A 6/2004
(Continued)

OTHER PUBLICATIONS

English language translation of SU 1674856 which originally published on Sep. 7, 1991.*
(Continued)

*Primary Examiner* — David A Rogers
(74) *Attorney, Agent, or Firm* — Curatolo Sidoti Co., LPA; Joseph G. Curatolo; Salvatore A. Sidoti

(57) ABSTRACT

An oral aroma sampling device includes a mouthpiece which defines an in-mouth surface and an external surface, the in-mouth surface bearing a delivery conduit, and the external surface bearing a manifold in communication with the delivery conduit, the manifold bearing a plurality of capillaries, each of which capillary is the conduit for an aroma substance, the mouthpiece additionally comprising a breathing conduit passing from the external surface to the in-mouth surface. The device is useful as part of a retronasal testing apparatus, which allows a large variety of flavor combinations to be tested quickly and efficiently.

10 Claims, 1 Drawing Sheet

(56) References Cited

U.S. PATENT DOCUMENTS

| | | | | |
|---|---|---|---|---|
| 2,905,049 | A | * | 9/1959 | Laube .............................. 352/85 |
| 2,957,476 | A | * | 10/1960 | Freeman ........................ 433/88 |
| 3,731,675 | A | * | 5/1973 | Kelly ............................ 601/164 |
| 3,902,851 | A | * | 9/1975 | Dravnieks .................... 73/23.34 |
| D283,158 | S | * | 3/1986 | Jackson ...................... D24/176 |
| 4,850,371 | A | * | 7/1989 | Broadhurst et al. .......... 600/532 |
| 5,104,315 | A | * | 4/1992 | McKinley ...................... 433/80 |
| 5,313,821 | A | * | 5/1994 | Bett et al. ..................... 73/23.34 |
| 5,513,634 | A | * | 5/1996 | Jackson .................. 128/207.18 |
| 5,610,674 | A | * | 3/1997 | Martin ............................ 352/85 |
| 5,949,522 | A | * | 9/1999 | Manne ............................ 352/85 |
| 6,067,842 | A | * | 5/2000 | Gygax et al. ................. 73/23.34 |
| 6,145,503 | A | * | 11/2000 | Smith ...................... 128/202.16 |
| 6,244,865 | B1 | * | 6/2001 | Nelson et al. ................. 433/140 |
| 6,257,238 | B1 | * | 7/2001 | Meah ............................ 128/859 |
| 6,338,715 | B1 | * | 1/2002 | Hayes et al. .................. 600/303 |
| 6,595,037 | B2 | * | 7/2003 | McGinley .................... 73/23.34 |
| 6,803,987 | B2 | * | 10/2004 | Manne ............................ 352/85 |
| 6,842,218 | B1 | * | 1/2005 | Manne ............................ 352/85 |
| 6,893,259 | B1 | * | 5/2005 | Reizenson ...................... 433/29 |
| 6,935,857 | B1 | * | 8/2005 | Farrell ............................... 433/6 |
| 7,601,297 | B2 | * | 10/2009 | Gygax et al. ...................... 422/5 |
| 8,295,529 | B2 | * | 10/2012 | Petersen et al. ................ 381/374 |
| 8,820,320 | B2 | * | 9/2014 | Filipi et al. ................ 128/200.26 |
| 8,973,573 | B2 | * | 3/2015 | Filipi ........................ 128/200.26 |
| 2002/0151871 | A1 | * | 10/2002 | Gaiser et al. ................... 604/510 |
| 2003/0015198 | A1 | * | 1/2003 | Heeke et al. ............... 128/204.18 |
| 2006/0282010 | A1 | * | 12/2006 | Martin et al. .................. 600/560 |
| 2007/0006878 | A1 | * | 1/2007 | Mackey et al. ........... 128/200.26 |
| 2007/0225570 | A1 | * | 9/2007 | Manishen ..................... 600/237 |
| 2009/0038555 | A1 | * | 2/2009 | Reese ........................... 119/174 |
| 2009/0123886 | A1 | * | 5/2009 | Vaska ............................. 433/27 |
| 2009/0228081 | A1 | * | 9/2009 | Perez ............................ 607/94 |
| 2013/0239657 | A1 | * | 9/2013 | Henry ........................ 73/23.34 |
| 2014/0163325 | A1 | * | 6/2014 | Hartston ...................... 600/205 |
| 2014/0275784 | A1 | * | 9/2014 | Joyce ........................... 600/114 |
| 2014/0276170 | A1 | * | 9/2014 | Hestness et al. .............. 600/531 |

FOREIGN PATENT DOCUMENTS

| | | |
|---|---|---|
| SU | 1674856 A1 | 9/1991 |
| WO | WO 2012/117935 A1 | 9/2012 |

OTHER PUBLICATIONS

GB Search Report No. 1212503.5, mailed Nov. 9, 2012.

* cited by examiner

RETRONASAL DEVICE AND METHOD

The present application claims the benefit of the filing date, pursuant to 35 U.S.C. §119(e), of U.S. Provisional Application for Patent Ser. No. 61/652,623, filed May 29, 2012, incorporated herein by reference.

This disclosure relates to retronasal testing, and a device and a method for such testing.

The testing of flavors has traditionally been carried out by a tester actually tasting a sample delivered by mouth, generally by drinking (if liquid) or eating (if solid). There are a number of problems with this approach, one being that the means of providing the sample (cup, spoon, spatula, fluid, food) also contacts the tongue, and can influence the perception of taste. A further problem is that there is a limit to the number of samples a tester can evaluate as a result of carry-over effects (lingering sensation in the mouth or nose) and satiety. The presence of either phenomenon makes it increasingly difficult for a tester to distinguish product differences.

One suggested way of avoiding this has been orthonasal testing, that is, supplying flavors to the nose rather than to the mouth. It is well known that a substantial element of flavour perception actually comes from the odor, and it has been suggested that orthonasal testing can be used to give an approximation of the perception of foods or beverages when evaluated by mouth. Moreover, because of the small quantities involved and the means of delivery (through a mask applied to the nose or through sniffing from a sniffing port or bottle), carry-over effects and satiety are substantially minimized or avoided, and a tester can test many more flavors than is possible with the traditional taste test.

However, the orthonasal methods hitherto described and tested deliver only an approximation of the flavour sensation experienced by tasting, and a more accurate impression is desirable.

It has now been found that these drawbacks may be substantially overcome, and flavours can be accurately assessed retronasally, by means of a particular apparatus and associated method. There is therefore provided an oral aroma sampling device, comprising a mouthpiece which comprises an in-mouth surface and an external surface, the in-mouth surface bearing a delivery conduit, and the external surface bearing a manifold in communication with the delivery conduit, the manifold bearing a plurality of capillaries, each of which capillary is the conduit for an aroma substance, the mouthpiece additionally comprising a breathing conduit passing from the external surface to the in-mouth surface.

There is additionally provided a method of retronasal testing of aroma substances, comprising (a) providing an aroma substance-providing apparatus and an oral aroma sampling device, the aroma substance-providing apparatus comprising a plurality of reservoirs of aroma substances each with a capillary delivery tube leading to the delivery apparatus, and (b) actuating the aroma substance-providing apparatus to provide the aroma substances to the delivery apparatus.

There is further provided a retronasal testing apparatus, comprising:

(a) an aroma substance-providing apparatus comprising a plurality of reservoirs of aroma substances each with a capillary delivery tube; and (b) an oral aroma sampling device as hereinabove described, which receives the capillary delivery tubes.

The oral aroma sampling device of this disclosure comprises the following elements:
   a mouthpiece;
   a manifold with delivery conduit extending therefrom through the mouthpiece and into the mouth;
   a breathing conduit.

The mouthpiece is a piece of material shaped to fit comfortably within a tester's mouth and be comfortably held there. It can therefore be of any suitable shape or configuration, or of any suitable material. This will be determined by whether the mouthpiece is a single-use or multiple-use mouthpiece, as in the latter case, it should be made of material able to be repeatedly sterilised. A typical suitable material is an elastomeric silicone rubber. However, any suitable material may be used, and the skilled person can readily provide a suitable material by the simple application of the skill of the art.

A typical suitable shape comprises a cylinder having an in-mouth end and an external end, from the in-mouth end of which extend two elastomeric diametrically-opposed elongate pieces adapted to fit against the inside of the tester's mouth and apply gentle pressure to hold the mouthpiece comfortably in place. However, again, this is only one possibility and the skilled person can easily provide a suitable shape or configuration.

The manifold is mounted externally, that is, in, on or adjacent to the external surface. It may, for example, be directly affixed to the external surface, or joined thereto by a suitable member. Alternatively, it may be encased within that part of the mouthpiece that is outside the mouth. This is a useful embodiment if the manifold is made of a breakable material, such as glass, in that it can offer some protection, especially if the material of the mouthpiece is resilient, such as a silicone.

From the manifold, there extends through the mouthpiece into the mouth a delivery conduit, typically a tube, whose function is to transport the aroma substance. This delivery conduit may be made of any suitable material and may be of any desirable length. In a particular embodiment, it may be removable and replaceable.

The mouthpiece is additionally equipped with a breathing conduit that allows direct communication of the mouth with the atmosphere. This allows the tester to breathe normally while testing, thus conferring the ability to test samples consecutively without removing the mouthpiece. The conduit may take any desired form. For example, it may be simply a conduit formed in the mouthpiece and extending from the external surface to the in-mouth surface, or it may have the form of a tube, optionally removable, extending through the mouthpiece. The placement of the conduit is not critical; it may, for example, pass through the manifold, or it may bypass it completely.

The manifold is additionally provided with a plurality of capillaries, whose function is to convey the individual aroma substances to the manifold for mixing and conveying to the mouth through the delivery conduit. The number and material of these capillaries is entirely dependent on the number of individual aroma substances that need to be conveyed, and the skilled person can easily provide the appropriate type and number.

In a further embodiment, the oral aroma sampling device comprises an additional conduit for the conveyance of liquid aroma or gustatory substances to the mouth. This typically has the form of a tube that passes through the mouthpiece, bypassing the manifold, the end remote from the mouthpiece being attached to a supply of liquid aroma or gustatory substances and associated pumping and metering equipment. It is sometimes desirable that a tester also receive a liquid sample in addition to a vapour-phase sample, and this conduit enables this.

The individual capillaries are in turn connected to individual reservoirs of aroma substances. These sources, in turn, form part of an aroma substance-providing apparatus. This is an apparatus that causes the aroma substances to move from the reservoirs in the desired selection and quantity to the oral sampling device. This may be achieved by any desirable means. For example, the reservoirs may be made of an elastic substance resistant to the particular substance, such as silicone rubber, and the aroma substance being caused to move by exerting pressure on the reservoir, by simply squeezing, or by activating a device that squeezes the reservoirs. In another variant, the reservoirs may be cylindrical and rigid, and having therein a plunger at the end remote from the capillary connection, such that the plunger can be urged towards the capillary connection in the manner of a pump. The skilled person can readily think of many other variants, all of which fall within the scope of this disclosure.

In a particular embodiment, the aroma substance-providing apparatus also comprises a control unit adapted to provide a required quantity of aroma substances from specified reservoirs. Thus, specifically desired values for each aroma substance may be entered into the unit and it will then supply those substances to the oral sampling device in the desired quantities. In a further embodiment, this unit may be programmable, such that a series of values representing different combinations may be entered and these then delivered to the oral sampling device in a desired order and at a desired interval. This allows an entire program to be entered.

In a particular embodiment, the oral aroma sampling device is used as part of a retronasal testing apparatus. Such an apparatus comprises an aroma substance-providing apparatus comprising a plurality of reservoirs of aroma substances each with a capillary delivery tube and a control unit adapted to cause the provision of a required quantity of aroma substances from specified reservoirs. Typical examples of such apparatus are the VAS™ and MiniVas™ apparatuses of Givaudan Flavors Corp. The combination of such apparatus with an oral aroma sampling device of the type hereinabove described provides a uniquely useful tool for the retronasal testing of flavor substances. The disclosure therefore also provides a method of retronasal testing of aroma substances, comprising
  (a) providing an aroma substance-providing apparatus and an oral aroma sampling device, the aroma substance-providing apparatus comprising a plurality of reservoirs of aroma substances each with a capillary delivery tube leading to the delivery apparatus and a programmable control unit adapted to cause the provision of a required quantity of aroma substances from specified reservoirs and the oral aroma sampling device comprising an oral aroma sampling device as hereinabove described,
  (b) programming the control unit to cause the provision of the desired types and quantities of aroma substances to the delivery apparatus; and
  (c) actuating the delivery apparatus to provide the aroma substances to the delivery apparatus.

The use of the oral aroma sampling device hereinabove described, especially as part of a retronasal testing apparatus as hereinabove described, provides a testing facility of considerable versatility and usefulness. With it, a tester can comfortably test considerably more samples than can a tester using the methods known to the art, thereby more quickly providing useful information to flavor formulators.

The disclosure is further described with reference to the accompanying drawings, which depict particular embodiments, and which are not to be construed as limiting the disclosure in any way.

Figure 1:
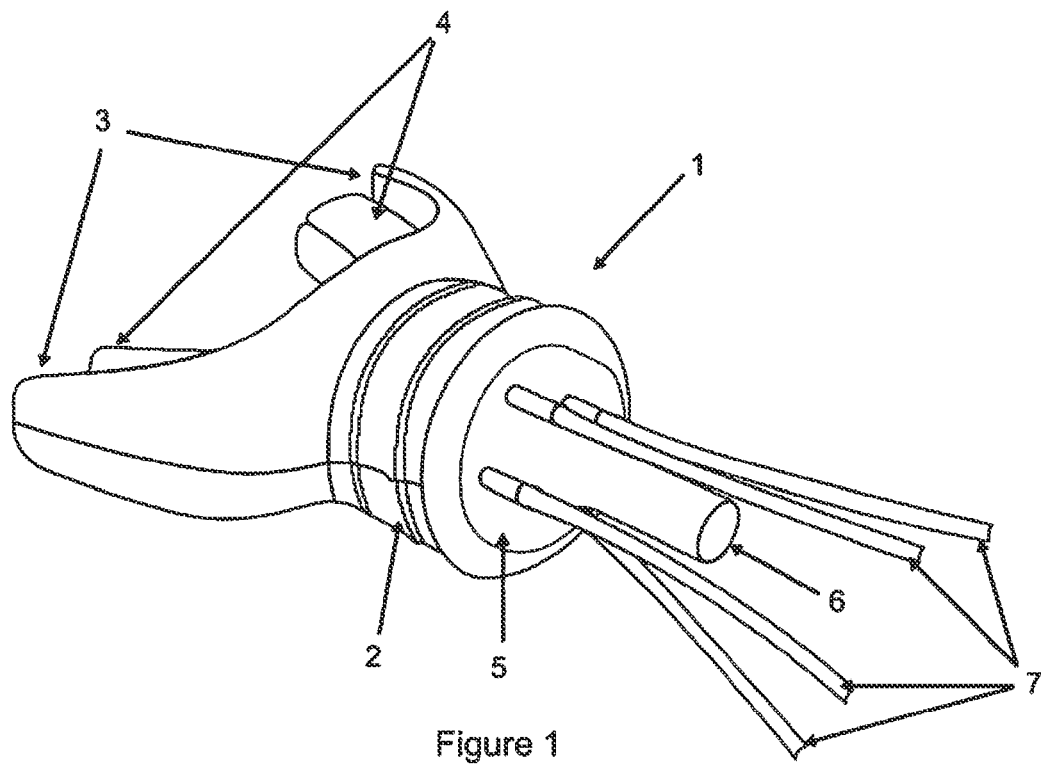
FIG. 1 is a perspective view of a particular embodiment.
Figure 2:
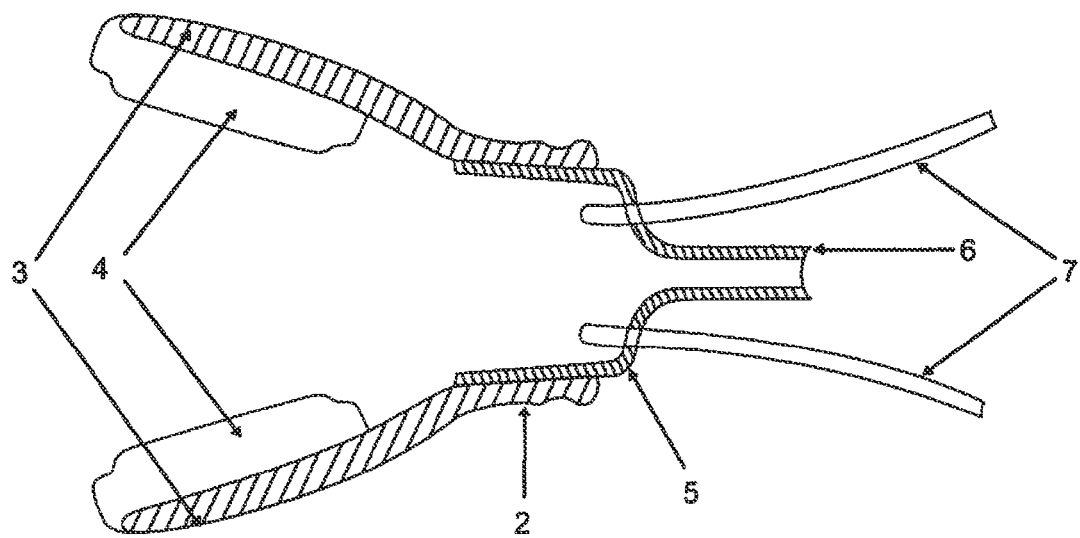
FIG. 2 is a longitudinal horizontal cross-section of the embodiment of FIG. 1.

An oral aroma sampling device, generally indicated as 1 comprises a hollow cylindrical portion 2 having cheek-engaging flaps 3 at that end that goes into a mouth. These cheek-engaging flaps are equipped on their inward faces with bite bars 4, adapted to be held between the teeth. The portions 2, 3 and 4 are molded as a single piece from a resilient silicone resin. Into the hollow cylinder is fitted a manifold 5, of glass, this being retained in place by resilient pressure exerted on the manifold 5 by the cylindrical portion 2, the relative diameters and materials being selected to permit this. The manifold is equipped with a breathing tube 6, which is integral with the manifold. Into the manifold is connected a plurality of capillary tubes 7, each leading to individual reservoirs in a metering and pumping device, such as the Givaudan VAS™ apparatus (not shown).

In operation, a tester inserts the cheek-engaging flaps 3 into the mouth, and they with their integral bite bars 4 enable the device to be held firmly but comfortably in place, while the breathing tube 6 allows normal breathing. An operator of the metering device can decide on a particular aroma to be tested and program into the metering device the necessary ingredients and proportions to provide the desired aroma. The individual ingredients travel to the manifold 5, where they mix and provide the desired aroma to the tester. A series of such aromas can easily be supplied in sequence, without the tester becoming satiated.

While the aroma sampling device and method of retronasal testing have been described above in connection with certain illustrative embodiments, it is to be understood that other similar embodiments may be used or modifications and additions may be made to the described embodiments for performing the same function without deviating therefrom. All embodiments disclosed are not necessarily in the alternative, as various embodiments may be combined or subtracted to provide the desired characteristics. Therefore, the device and method should not be limited to any single embodiment, but rather construed in breadth and scope in accordance with the recitations of the attached claims.

We claim:

1. An oral aroma sampling device, comprising a mouthpiece which comprises an in-mouth surface and an external surface, the in-mouth surface bearing a delivery conduit, and the external surface bearing a manifold in communication with the delivery conduit, the manifold bearing a plurality of capillaries, each of which capillary is the conduit for an aroma substance, wherein each capillary is connected to a reservoir of aroma substance, the mouthpiece additionally comprising a breathing conduit passing from the external surface to the in-mouth surface.

2. The oral aroma sampling device according to claim 1, in which the device comprises an additional conduit for the conveyance of liquid aroma or gustatory substances to the mouth.

3. The oral aroma sampling device according to claim 1, in which the individual reservoirs form part of an aroma substance-providing apparatus.

4. The oral aroma sampling device according to claim 3, in which the aroma substance-providing apparatus comprises a control unit adapted to provide a required quantity of aroma substances from specified reservoirs.

5. The oral aroma sampling device according to claim 4, in which the control unit is programmable.

6. A retronasal testing apparatus comprising:
(a) an aroma substance-providing apparatus comprising a plurality of reservoirs of aroma substances each with a capillary delivery tube; and
(b) an oral aroma sampling device, which receives the capillary delivery tubes;
the oral aroma sampling device comprising a mouthpiece which comprises an in-mouth surface and an external surface, the in-mouth surface bearing a delivery conduit, and the external surface bearing a manifold in communication with the delivery conduit, the manifold bearing a plurality of capillaries, each of which capillary is the conduit for an aroma substance, the mouthpiece additionally comprising a breathing conduit passing from the external surface to the in-mouth surface.

7. The retronasal testing apparatus of claim 6, in which the device comprises an additional conduit for the conveyance of liquid aroma or gustatory substances to the mouth.

8. The retronasal testing apparatus of claim 6, in which each capillary is connected to one of the plurality of reservoirs of aroma substances.

9. The retronasal testing apparatus of claim 6, in which the aroma substance-providing apparatus comprises a control unit adapted to provide a required quantity of aroma substances from specified reservoirs.

10. The retronasal testing apparatus of claim 9, in which the control unit is programmable.

\* \* \* \* \*